(12) United States Patent
Zhang et al.

(10) Patent No.: US 7,811,997 B2
(45) Date of Patent: Oct. 12, 2010

(54) COMPOSITION CONTAINING TOTAL TRITERPENOID SAPOGENINS EXTRACTED FROM BAMBOO, AND THE PREPARATION METHOD AND USE THEREOF

(75) Inventors: Ying Zhang, Food Bld., Huajiachi Campus of Zhejiang Univ., 268 Kaixuan Road, Hangzhou, Zhejiang Province (CN) 310029; Xiaoqin Wu, Hang Zhou (CN); Zhuoyu Yu, Hang Zhou (CN); Yunlong Zhu, Shanghai (CN); Lingen Chen, Shanghai (CN); Shenggen Lou, Shanghai (CN)

(73) Assignees: Ying Zhang, Baiyur Villa, Hangzhou, Zhejiang (CN); Xiaoyi Chen, Shanghai (CN)

( * ) Notice: Subject to any disclaimer, the term of this patent is extended or adjusted under 35 U.S.C. 154(b) by 642 days.

(21) Appl. No.: 10/538,463

(22) PCT Filed: Apr. 28, 2003

(86) PCT No.: PCT/CN03/00309

§ 371 (c)(1),
(2), (4) Date: Nov. 23, 2005

(87) PCT Pub. No.: WO2004/052383

PCT Pub. Date: Jun. 24, 2004

(65) Prior Publication Data

US 2006/0148733 A1    Jul. 6, 2006

(30) Foreign Application Priority Data

Dec. 10, 2002   (CN)  ............................... 02 1 54401

(51) Int. Cl.
*A01N 45/00*    (2006.01)
*A61K 31/704*    (2006.01)
*A61K 36/899*    (2006.01)
*C07H 15/24*    (2006.01)

(52) U.S. Cl. ........................... 514/26; 514/25; 514/23; 514/169; 514/33; 536/5; 536/18.1; 424/750

(58) Field of Classification Search .................. 514/26, 514/25, 23, 169, 33; 536/5, 18.1; 424/750; 54/33

See application file for complete search history.

(56) References Cited

U.S. PATENT DOCUMENTS 6,387,417 B1 *   5/2002   Iwai ........................... 424/729

FOREIGN PATENT DOCUMENTS

| EP | 1122259 A2 * | 8/2001 |
| JP | A.57039753 | 3/1982 |
| JP | A.3251518 | 11/1991 |

OTHER PUBLICATIONS

Ohmoto et al. (Shoyakugaku Zasshi (1974), 28(1), pp. 1-6) (Abstract Sent).*
Gura (Science, 1997, 278 (5340):1041-1042).*
Jain (Sci.Am., i994, 271:58-65).*
CurU (Crit. Rev. in Oncology/Hematology, 1993, 14:29-39).*
Kobayashi et al. (Bull Fac Agr, Meiji Univ (115): 39-44, 1998).*

* cited by examiner

*Primary Examiner*—Shaojia Anna Jiang
*Assistant Examiner*—Michael C Henry
(74) *Attorney, Agent, or Firm*—Yuan Qing Jiang (57) ABSTRACT

The invention relates to a composition containing total triterpenoid sapogenins extracted from bamboo, the preparation method and use thereof. These total triterpenoid sapogenins are extracted from many parts of bamboo such as bamboo shavings in Gramineae by $CO_2$ Supercritical Fluid Extraction technique. In the extract, the content of total triterpenoid sapogenins is 10-90%, while the contents of friedelin and lupenone are 5-35% and 1-10%, respectively. The extract in the invention has good physiological and pharmacological activities such as anti-free radical, anti-oxidation, anti-tumor and anti-hypertension. It can be used in medicines or functional foods for the treatment or prevention of cardiovascular and cerebrovascular diseases and tumor. It is also useful in cosmetics field.

4 Claims, 6 Drawing Sheets

COMPOSITION CONTAINING TOTAL TRITERPENOID SAPOGENINS EXTRACTED FROM BAMBOO, AND THE PREPARATION METHOD AND USE THEREOF

FIELD OF THE INVENTION

This invention relates generally to a composition containing total triterpenoid sapogenins extracted from bamboo, as well as the preparation method and use thereof. These triterpenoids are extracted from bamboo using $CO_2$ Supercritical Fluid Extraction (SFE) technique. Furthermore, it is a mixture mainly comprising pentacyclic triterpenoids of friedelin, lupenone and their homologous compounds. It can be used in medicines or functional foods for the treatment or prevention of cardiovascular and cerebrovascular diseases and tumor. It is also useful in cosmetics field.

BACKGROUND

Bamboo belongs to Bambusoideae family in Gramineae. There are about 70 genera, over 1200 species of bamboo on the earth. The area of bamboo grove is approximately 20,000,000 hectare all over the world. China is one of main bamboo producing countries in the world. In China, there are about 40 genera, over 400 species of bamboo (i.e. one-third of world bamboo resources) and the area of bamboo grove is approximately 4,000,000 hectare. Meanwhile, there are over 50 species of bamboo in *Phyllostachys* Sieb. et Zucc all over the world. Many species of them have been produced in China except minority varieties. Furthermore, the area of bamboo in *Phyllotachys pubescens*, which has the highest economic utility value in bamboo kingdom, is about 2,500,000 hectare (i.e. more than 90% of world bamboo yields in *Phyllotachys pubescens*) in China.

Bamboo is one of the most valuable natural plants all over the world. Bamboo is praised as "Gold of the Poor" for its high economic value so that it acts as an important ingredient of forest resources. Meanwhile, bamboo has widespread ecological environmental effects and social benefits. Researches on the available compositions and biological effects of bamboo are mainly in China and Japan. Besides, a few of similar researches are conducted in India, Brazil, USA and Korea. Study objects of bamboo species in various countries have notable local characteristics. Therefore, scientists usually choose special bamboo species with domestic characteristics for study.

A kind of herbaceous bamboo in Subgen. Sasamorpha, Subgen. Sasa and Sasa Makino et shbata (i.e. Sasa albomarginta Makino & Shibata in Latin or bamboo grass in English) has been systematically studied and a series of national patents have been filed in Japan since 1970s. A few of researches related to bamboo species in *Phyllostachys* after 1990. For example, the extract of tender stems of bamboo in *Phyllostachys*, which is obtained by solvent extraction, can be added into the feed for animals such as poultry, livestock, shellfish, pets and experimental animals, etc (Wataru, S. Healthful feed containing bamboo extract, JP. Pat. 57,074,049, filed in 1980). In another patent application filed in 1980 (Healthful feed containing bamboo extract, JP. 57,039,753), it was disclosed that the fragmentized tender stems of bamboo in *Phyllostachys* were extracted 2 weeks by methanol, ethanol, chloroform, benzene or hot water under the normal temperature, or they were put into containers, heated up to 180° C. by steams, cooled after distillation, so that a mixture of essential oil and water was produced. Said concentrated products under decompression can be added into various foods. Besides, the bamboo extract obtained by dry or steam distillation has a therapeutic effect on hemorrhoids. Different active portions separated by silica gel column have different healthy effects such as hemorrhoids therapy, anti-hypertension and relaxation. Furthermore, the hemorrhoids therapeutic portion has prominent effects when orally or topically administrated (Wataru, S. Production of bamboo extract having effect for hemorrhoids, JP. Pat. 1982, No. 57,038,721).

It has been reported that the extract of bamboo leaves and its lignin have anti-tumor activities (Kuboyama, N. et al. Anti-tumor activity of bamboo leaf extracts, JPN J. Pharmacol., 1979, 29(SUPPL.): 170; Anti-tumor activities of bamboo leaf extracts and its lignin, Folia Pharmacol. JPN, 1981, 77(6): 579-596). Besides, the extract solution of bamboo leaves was used in periodontal therapy (Sato, T. et al. The use in periodontal therapy of a bamboo leaf extract solution, Nippon Shishubyo Gakkai Kaishi, 1986, 28(2): 752-757). The effective compositions extracted from bamboo in *Phyllostachys* such as *P. bambusoides*, *P. pubescens* and *P. nigra var. henonis.* can inhibit the growth of poly-dandruff fungus and the lipid peroxidation, prevent the skin aging process and stabilize products (Kenji, M. et al. Skin, scalp and hair agent containing component of suppressing growth of dandruff fungus extracted from bamboo, JP. Pat. 1991, No. 3,251,518). Therefore, many different kinds of bamboo extracts have been studied and applied in many fields, such as the identification of the anti-microbial active component of 2,6-dimethoxyl p-benzoquinone, the preparation of deodorant, the application of anti-microbial activity and the exploitation of meat additives, etc (Nishina, A. et al. J. Agric. & Food Chem., 1991, 39(2): 266-269; Takatoshi, K. JP. Pat. 9,094,290; Yamanaka, Satoshi. et al. Anti-microbial activity of bamboo dry distillate and its application, Gekkan Fudo Kemikaru, 1998, 14(9): 57-60; Akimitsu, M. JP. Pat. 11,346,719). The anti-oxidative activity of tricin and taxifolin, which are two kinds of anti-oxidative compounds extracted from bamboo shoot sheath, approximately corresponds to 10% and 1% of that of α-tocopherol, respectively (Sakai, K. Isolation of anti-oxidative compounds from bamboo shoots sheath, Nippon Shokuhin Kagaku Kaishi, 1999, 46(7): 491-493).

China is praised as "Bamboo Kingdom". Bamboo not only has centuries-old edible history in China (C. S. Hu et al. Development history of bamboo as medicine and food, Journal of Bamboo Research, 1999, 18(1): 27-31), but also is a kind of important resource on the exploitation of Chinese medicine and health food. Therefore, it has an important significance in the modernization of Chinese medicine. In China Chinese Medicine Resource Highlights, there are 32 species of bamboo in 10 genera among 12,694-recorded kinds of Chinese medicine, while there are about 5 species of bamboo plants in Pharmacopoeia of the P. R. China (1990 Edition). Different parts of bamboo, such as bamboo leaf, bamboo rhizome system, *Caulis bambusae* in Taeniam (bamboo shavings), *Succus bambusae* (bamboo juice), *Fructas bambusae* (bamboo fruit), bamboo poles, *Concretionsilicea bambusae* (concretionin bamboo stem), *Shiraia bambusicola* Henn. (tabasheer), bamboo shoots, *Amomum villosum bambusae*, *Omphalia lapidescens schroet*, membranae bambusae (mambranein bamboo stem), bamboo essence, *Rhizomys sinensis* Gray. and *Xylocopadis similis* Lep., have different therapeutic effects (Z. Y. Zhang et al. Potential of bamboo on the exploitation of Chinese Medicine and health food, Modernization of Traditional Chinese Medicine, 2000, 2(3): 54-56).

Abundant researches on bamboo components and bioavailability have been studied in China. Furthermore, bamboo-leaf flavonoids have been studied systematically and thoroughly by applicant of the invention. Recently, the extract of bamboo leaves (Ebl$_{971}$), a kind of natural bioflavone product that is extracted from the most abundant bamboo species (i.e. *Phyllostachys* Sieb. et Zucc.) in domestic bamboo resources, has been exploited by applicant. This natural product mainly contains four kinds of C-glycosyl flavones, i.e. orientin, homoorientin, vitexin and isovitexin (Y. Zhang. Natural functional extract of bamboo leaves: bamboo leaf anthoxanthin, China Food Additives, 2002, (3): 54-58, 66). Ebl$_{971}$ has many kinds of biological effects such as anti-free radical, anti-oxidation, anti-senescence, anti-bacteria, anti-virus and preventing cardiovascular and cerebrovascular disorders and senile degenerative diseases, etc (Y. Zhang et al. Studies on antioxidative fraction in bamboo leaves and its capacity to scavenge active oxygen radicals, Journal of Bamboo Research, 1996, 15(3): 17-24; Y. Zhang et al. Experimental studies on anti-aging effect of the leaf-extract of *P. nigra* var. *henonis*, Journal of Bamboo Research, 1997, 16(4): 62-67; Y. Zhang. Determination of SOD-like activity of bamboo leaf extract by pyrogallol autooxidation, Food Science, 1997, 18(5): 47-49; Y. Zhang et al. The bio-antioxidative activity of functional factors in bamboo leaves, in: Proceedings of the 3rd International Conference of Food Science and Technology, Oct. 19-23, 1997, Davis, U.S. Ed. Whitaker, J. R. Food and Nutrition Press, 1998, pp 266-273; Y. Zhang. Comprehensive study on SOD-like activity of bamboo leaf extract, Journal of Chinese Institute of Food Science and Technology, 1998, 2(2): 62-66; Y. Zhang et al. Study on the relationship between the structure of flavonoids and their scavenging capacity on active oxygen radicals by means of chemiluminescence, Natural Product Research and Development, 1998, 10(4): 26-33; Y. Zhang et al. The bio-antioxidative activity of functional factors in bamboo leaves, Acta Nutrimenta Sinica, 1998, 20(3): 367-371; C. Hu, Y. Zhang and Davis D. K. Evaluation of antioxidant and prooxidant activities of bamboo *Phyllostachys nigra* var. *henonis* leaf extract in vitro, J. Agric. Food Chem., 2000, 48(8): 3170-3176). Ebl$_{971}$ has abundant material resources, definite functional factors, good edible safety (actually no toxicity), high efficient and stable preparation quality (water-, heat- and acid-resistance, etc) and fresh and sweet bamboo flavor so that it has made a figure in the field of natural functional food additives and medical health food recently. Furthermore, China Patent Office issued two patents for invention to applicants in 2000 and 2001, respectively (Y. Zhang. The production method of flavonoid extract and powder extracted from bamboo, CN. Pat. ZL 98 1 04564.2; Y. Zhang. A kind of health beer fortified by the bamboo extract-leaf-flavonoids, CN. Pat. ZL 98 1 04563.4). Nearly all the bamboo researches in China are aimed at *Phyllostachys* Sieb. et Zucc., especially *P. nigra* var. *henonis*, *P. pubescens* and *P. bambusoides* Sieb. et Zucc.

Bamboo researches in India relate to nutrition of bamboo fruits, processing of bamboo shoots, manufacture of bamboo fibers and feed application of bamboo leaves. The objects of these researches mainly relate to bamboo species in *Bambusa* and *Dendrocalamus* genus with local resource characteristics.

Brazil locates in bamboo zones of South America. The main species of bamboo in Brazil are cluster bamboo in *Bambusa* and *Dendrocalamus* genus. Brazilian scientists have ever detected carcinogenic compounds from *Dendrocalamus giganteus* Munro. Nevertheless, they can be removed by different kinds of processing methods (Ferreira, V. L. P. et al. Elimination of cyanogenic compounds of bamboo shoots *Dendrocalamus giganteus* Munro by different processes, Rev Esp Cienc Tecnol Alimentos, 1992, 32(2): 175-184).

There is nearly no bamboo in the main land of U.S. However, with the continuous cognition of healthy effects of bamboo products, some research institutes began the research on bamboo products such as bamboo shoots. The department of food and nutrition in Purdue University reported the effect on lowering serum cholesterol level in rats by bamboo shoots in the U.S. Federal Conference of Experimental biology (Anaheim, Calif., U.S.) (Story, J. A. et al. Bamboo shoots lower serum cholesterol in rats, FASEB (Fed Am Soc Exp Biol) J, 1992, 6(5): A1653). Furthermore, the systematic research on the hypocholestolemic effect of bamboo shoots both in vivo and in vitro by He in Rutgers University has suggested that phytosterols play a key role in this effect (Y. H. He. The hypocholestolemic effect of bamboo shoots in vivo and in vitro (*Phyllostachys edulis*, Phytosterols), Dr. Paper of Rutgers University, 1998).

It can be inferred from bamboo extract researches all over the world that the extraction methods of bamboo mainly relate to water extraction, organic solvent extraction and steam distillation. However, studies on the chemical research of active compositions and the structure relationship between compositions and their physiological and pharmacological activity are extremely limited.

The plant resources of this invention relate generally to complete bamboo stools, including stems, roots, leaves, branches and shoots, but mainly relate to bamboo bark the obtained portion of which is similar with bamboo shavings recorded in Dictionary of Traditional Chinese Medicine (Vol. 1, China Medical Science and Technology Press, 1993, pp 2137-2139). Furthermore, the source and extent of bamboo species in the invention are also similar to those recorded in this dictionary, especially the bamboo in *Phyllostachys* Sieb. et Zucc.

Bamboo shavings recorded in Dictionary of Traditional Chinese Medicine (Syn. with bamboo bark recorded in Synopsis Prescriptions of the Golden Chamber, green bamboo shavings recorded in Divine Husbandman's Classic of Materia Medica, bamboo bark in *P. nigra* var. *henonis* recorded in Divergent Records, bamboo shavings in *P. nigra* var. *henonis* recorded in Materia Medica of Food Therapy, Ma ba recorded in Herb Prescriptions or inferior outer of bamboo recorded in Shanghai Service Chinese Herb Medicine) are external or intermediate layers of some bamboo stems of *Phyllostachys, Bambusa* or *Dendrocalamus* genus in Gramineae. Certified products of bamboo shavings can be divided into two categories, *Phyllostachys nigra* var. *henonis* (Bean) Stapf. (*P. henryi* Rendle) and *Phyllostachys aurea* Carr. ex A. and *C. Riviere*. Furthermore, many other kinds of bamboo also can be used as sources of bamboo shavings such as *P. glauca* McClure, *P. makinoi* Hayata, *P. nidularia* Munro, *P. viridis* (Young) McClure, *Bambusa tuldoides* Munro, *B. pervariabilis* McClure, *B. chungii* McClure [*Lingnania chungii* (McClure) McClure], *Dendroclamopsis beecheyana* (Munro) Keng f. var. *pubescens* (P. F. Li) Keng (*Sinocalamus beecheyana* var. *pubescens* P. F. Li) and *Dendrocalamus affinis* Rendle (*Sinocalamus affinis* (Rendle) McClure). On one hand, it can be inferred from bamboo distributions in China that the bamboo species distributed in Yangtze River Basin are mainly *P. nigra* var. *henonis*, a kind of scattered bamboo, and the following *P. aurea* Carr. ex A. & *C. Riviere, P. makinoi* Hayata, *P. nidularia* Munro, *P. glauca* McClure and *P. viridis* (Young) McClure, etc. On the other hand, the bamboo species distributed in Southwest and South Region of China are mainly *B. tuldoides* Munro, a kind of cluster bamboo, and the following *Sinocalamus beecheyana* var. *pubescens* P. F. Li, *B. chungii* McClure, *B. pervariabilis* McClure and *Sinocalamus affinis* McClure (*Dendrocalamus affinis* Rendle), etc.

Bamboo shavings, which act as a kind of clinical Chinese traditional medicine, have mainly been used in many symptoms such as gastropyretic vomiting and chest diaphragm annoyance, etc. Traditional roasting and preparing method of bamboo shavings is to remove impurities and cut it into segments or kneading agglomerate. They can be prepared after ginger juice stir-frying. This method is initially recorded in Divine Husbandman's Classic of Materia Medica and the efficacy has been recorded in materia medica of past dynasties. Examples are showed as follows: (i) Bamboo shavings can be used to treat many symptoms such as over-stained relapse of exogenous febrile disease, infantile middle laryngeal abscess and female excessive fetal movement (S. Z. Li, Detailed Outline of Materia Medica). (ii) Bamboo shavings especially eliminate stomach heat and can be prescribed for deficient restlessness with polydipsia, gastric asthenia with vomiting, hiccup with bloody sputum and puerperal deficient restlessness (L. Zhang, Journey to Source of Materia Medica). (iii) Bamboo bark bolus can be prescribed for puerperal deficient restlessness with vomiting (Z. J. Zhang, Synopsis Prescriptions of the Golden Chamber). (iv) Sweet soup of bamboo shavings can be prescribed for puerperal endoasthenia and dysphoric fever with short breath in order to calm the middle (stomach and spleen) while mild soup of them can be used to puerperal deficient restlessness with headache, short breath and annoyance in order to cool stomach. Although the character of soup is sweet and slippery, it can promote defecation and urination so that nothing can be anxious about including exogenous pathogen (S. M. Sun, Prescriptions worth a Thousand Gold). (v) Bamboo shavings, which are dispersing herbs eliminating sthenia, cooling herbs eliminating heat or bitter herbs keeping the adverse energy downwards, are good prescriptions of eliminating pyretic cough and expelling stagnation. They can be mainly prescribed for cholic and gastric phlegmatic fever symptoms such as gastropyretic dysphagia, gastrasthenia retching, pyretic hiccup, phlegmatic fever with nausea, alcoholic injury vomiting, phlegmatic acid saliva, terrified and severe palpitation, cardiac restlessness and sleep dysphoria (S. X. Jia, Medicinal Ingredients Changes and Corrections). (vi) Bamboo shavings with a sweet, mild taste and a cold, slippery odor can be prescribed for many symptoms such as polydipsia restlessness, dysphagia with vomiting, pernicious vomiting, haematemesis and non-traumatic hemorrhage caused by pulmonary heat accumulation and nourishing loss involving lung meridian (G. X. Huang, Truthseeking Materia Medica).

Pharmacopoeia of the P. R. China (2002 Edition) declares that bamboo shavings originate from *Phyllostachys nigra* (Lodd.) Munro var. *henonis* (Mitf.) Stapf ex Rendle, *Bambusa tuldoides* Munro and *Sinocalamus beecheyanus* (Munro) McClure var. *pubescens* P. F. Li with a sweet-natured taste, a cold odor, lung distribution and stomach meridian. Bamboo shavings mainly can be prescribed for eliminating phlegm by cooling and eliminating dysphoria with stopping emesis. Furthermore, they can be used to treat the following symptoms: pyretic cough, gallbladder fire with sputum, dysphoric fever with vomiting, terrified palpitation with insomnia, apoplexy with phlegmatic coma, aphasia with stiff tongue, gastropyretic vomiting, pregnant pernicious vomiting and excessive fetal movement. However, the pharmacological details of Bamboo shavings are still unknown and the materials of functional evaluation are relatively absent because the componental and pharmacological study on bamboo shavings is seldom carried out in the traditional Chinese medicine. Although Dictionary of Traditional Chinese Medicine refers to some components in bamboo shavings that have inhibitory effects on cAMP phosphodiesterase (China Medical Science & Technology Press, Vol. 1, pp 2138), and they are identified as 2,5-dimethoxy-p-benzoquinone, p-hydroxybenzoaldehyde and syringaaldehyde. No documents have reported triterpenoids in bamboo shavings so far.

Nevertheless, the composition descriptions of *Herba Loophatheri* (Common Lopatherum Herb) in Chinese folk records relate to triterpenoids. However, this kind of Herba Loophatheri is the stem and leaf of *Lophatherum gracile* Brongn in Gramineae, which is a herbaceous perennid but doesn't belong to Bambusoideae family. It is cultivated in Zhejiang, Jiangsu, Hunan and Hubei Province in China. This kind of herb has the efficacy of eliminating dysphoria by cooling and promoting fluid production to induce diuresis with a sweet and mild taste, a cold odor and heart and kidney meridian. Furthermore, it can be used to treat many symptoms such as febrile polydipsia, hot urination, turbid stranguria, aphthous stomatitis and tongue abscess and gingival cyst. The stems and leaves of *Lophatherum gracile* Brongn mainly contain triterpenoids and sterols which are identified as arundoin, cylindrin, taraxerol, friedelin, β-sitosterol, stigmasterol, campesterol and taraxasterol while their aerial parts contain phenols, amino acids, organic acids and saccharides. Recently, Q. Chen conducted a systematic studies on the components of *Lophatherum gracile* Brongn. (Q. Chen et al. Chemical studies on the constituents of *Lophatherum gracile* Brongn., J. Shenyang Pharmaceutical Univ., 2002, 19 (1): 23-24). Eight compounds were identified as 4-hydroxy-3,5-dimethoxybenzaldehyde, trans-p-hydroxy cinnamic acid, tricin, tricin-7-O-β-D-glucosyl, vitexin, thymine, vanillic acid and adenine. Unfortunately, triterpenoids were not reported.

Most triterpenoids, which consist of 30 carbons, are considered a condensation compound of 6 isoprenes. Triterpenoids and their saponins, which are important biological active components in natural kingdom, can be divided into two categories, i.e., triterpenoid saponins and steroid saponins, according to their different chemical structures. Many kinds of triterpenoid saponins extracted from several important Chinese herbal medicine such as *Panax genseng, Panax notoginseng, Gynostemma pentaphyllum, Bupleurum, Astragalus, Polygala temuifolia, Phytolacca acinosa, Platycodon grandiflorum* and *Anemarrhena asphodeloides* have been studied systematically with the continuous advance in study methods of organic compounds in recent 30 years. Their biological activities and medicinal values have been recognized increasingly. These substances have many kinds of biological activities such as anti-bacteria, anti-virus, anti-tumor, anti-fertility, anti-inflammatory, anti-hyperlipidemia, anti-hypertension, anti-hyperglycemia and immunoregulation, etc. Further, triterpenoids have physiological activities in the cardiovascular system, nervous system, adrenal cortex system and enzymatic activity so that they have become an important investigated subject in the research of natural medicine (X. S. Yao. Natural Pharmaceutical Chemistry (3rd Edition), People's Medical Publishing House, 2001, 257-294; S. J. Wu et al. Recent research survey on pharmacological activities of saponins, World Notes on Phytopharmacy, 1994, 9(6): 246-252).

Generally, the number of pentacyclic triterpenoids is more than any other kinds of triterpenoids. They are mainly divided into the following four categories: oleanane, ursane, lupinane and friedelane. Among them, friedelane is derived from the translocation of oleanen hydroxymethyl group. *Tripterygium wilfordii*, which belongs to Celastraceae family, has a centuries-old history of folk pharmaceutical products in China. Recently, it has been widely applied in the clinic, especially in rheumatoid diseases because of its unique therapeutic effectiveness. Meanwhile, several kinds of triterpenoids including friedelane triterpenoids have been extracted from *Tripterygium wilfordii*. For instance, triptergone, a kind of triterpenoid extracted from the peeled root center of *Tripterygium wilfordii*, is a friedelane derivative without methyl group on position 25 and its chemical name is 3-hydroxy-25-nor-friedel-3,1(10)-dien-2-one-30-oic acid. More than 20 kinds of friedelane compounds or their degradation products have been extracted from *Kokona zeylanica* in Celastraceae family so far. Meanwhile, 11 compounds have been obtained from the stem bark of this plant and identified as friedel-3-one compounds by Leslie et al.

The extraction and separation method of triterpenoids can be generally divided into four categories: (i) The extraction is extracted by ethanol or methanol and triterpenoids are directly separated. (ii) The extraction is primarily extracted by alcohol solvents and divisionally extracted by petroleum ether, chloroform and acetic ester in turn and further separated. The triterpenoid compositions are mainly obtained from chloroform. (iii) Triterpenoids are separated by the preparation of derivatives. In other words, the extraction is extracted by ether, methylated by diazomethane and prepared as methyl ester derivatives, or it is prepared as acetyl derivatives by conventional acetylation and further separated. (iv) Triterpenoids are prepared after triterpenoid saponins hydrolyzation because many kinds of triterpenoids is present as saponins in plant materials. In other words, triterpenoid saponins are hydrolyzed and the hydrolysis products are extracted by organic solvents such as chloroform. Finally, triterpenoids are prepared. However, the extraction method of chemical solvents has many defects such as long operation, great solvent consumption and bad operational environment. Furthermore, the extract obtained by organic solvent extraction has unstable product quality, high contents of heavy metal and pesticide residue and low extraction yield.

SUMMARY

The purpose of this invention is to provide a composition, preparation method and application of total triterpenoid sapogenins extracted from bamboo.

In the first aspect, the invention provides a composition of total triterpenoid sapogenins extracted from bamboo. The content of total triterpenoid sapogenins in this composition is 10-90% as determined by vanillic aldehyde and perchloric acid colorimetry using friedelin as a standard, and the contents of friedelin and lupenone in this composition are 5-35% and 1-10% respectively as determined by GC-MS.

In a preferred embodiment, the content of total triterpenoid sapogenins is 40-80% and the contents of friedelin and lupenone are 15-25% and 3-6%, respectively.

In another preferred embodiment, the total triterpenoid sapogenins comprise pentacyclic triterpenoids of friedelin, lupenone and their homologous compounds. The total triterpenoid sapogenins are yellow or yellowish green powders with a melting point of 74-79 degree C. The IR spectrogram performed by potassium bromide shows characteristic absorption peaks in the wave numbers of 2917, 2849, 1716, 1463, 1382 and 720 $cm^{-1}$. The UV spectrogram dissolved by spectroscopic pure $CH_2Cl_2$ with a scan ranging from 300 to 700 nm shows a strong absorption in the wavelength of 412 nm, a sub strong absorption in the wavelength of 665 nm and a weak absorption in the wavelengths of 505, 535 and 605 nm.

In the second aspect, the invention provides a method for extracting total triterpenoid sapogenins from bamboo, comprising the steps of:

(a) mixing the material with the supercritical $CO_2$ fluid, thereby making the low-polar substances of bamboo such as free triterpenoids dissolve in $CO_2$ fluid, wherein the material is selected from the group consisting of poles, branches, leaves, shoots, shoot sheaths and roots of bamboo in Gramineae family or their mixture, and the extraction temperature is 50-65° C. and the pressure is 25-35 Mpa;

(b) changing the pressure of $CO_2$ fluid containing free triterpenoids to gasify $CO_2$, and separating the total triterpenoid sapogenins, wherein the separation temperature is 35-45° C. and the pressure is 5-10 Mpa.

In a preferred embodiment, the material is bamboo powder with the granularity of 10-20 meshes, an entrainer is used in step (a) in amount of 5-15% (v/v) of $CO_2$, $CO_2$ is recycled and the bamboo powder is circularly and dynamically extracted for 2-5 h.

In another preferred embodiment, the entrainer is selected from the group consisting of methanol, ethanol, acetone or the combination.

In another preferred embodiment, the bamboo is selected from *Phyllostachys, Bambusa* or *Dendrocalamus* genus.

In the third aspect, the invention provides the following applications of the composition of total triterpenoid sapogenins:

Total triterpenoid sapogenins and the friedelin monomer are useful to prepare (i) a new medicine or a Chinese and Western complex formulation used to prevent or treat hypertension, heart failure, myocardial ischemia, cerebral ischemia, senile dementia and carcinoma, and (ii) a functional food or a complex formulation used to prevent or treat cardiovascular and cerebrovascular diseases, and carcinoma.

Total triterpenoid sapogenins are useful as skin and hair care factors in the preparation of daily cosmetics such as skin cream, conditioning shampoo and bath foam, etc.

The pentacyclic triterpenoids of total triterpenoid sapogenins are useful to prepare medicines or functional food for preventing or treating cardiovascular and cerebrovascular diseases and carcinoma, or to prepare cosmetics.

DETAILED DESCRIPTION

This invention relates to an extraction method of triterpenoids extracted from the poles, branches, leaves and roots of bamboo in *Phyllostachys, Bambusa* or *Dendrocalamus* genus in Gramineae, especially from bamboo shavings in Gramineae by the $CO_2$ Supercritical Fluid Extraction (SFE) technique.

A specific mode for carrying out the invention is as follows:

The bamboo powder with the granularity of 10-20 meshes is put into the $CO_2$ supercritical kettle and then circularly and dynamically extracted by $CO_2$ SFE technique under the supercritical $CO_2$ condition modified or unmodified with entrainers in the pressure of 25-35 Mpa, the temperature of 50-65° C., and the extraction time of 2-5 h. Finally, the bamboo extract (hereinafter referred as $EZR_{2002}$) is obtained. Furthermore, the entrainers include organic solvents such as methanol, ethanol and acetone and their use level is 5-15% (v/v) $CO_2$.

The advantage of the invention is described as follows:

A group of bamboo sources mainly including pentacyclic triterpenoids about many kinds of physiological and pharmacological activities are provided. Furthermore, efficient extraction of total triterpenoid sapogenins in bamboo has been carried out successfully by the $CO_2$ SFE technique so that high accuracy and quality products have been obtained, while the main composition and the variation range of their content have also been investigated clearly. Meanwhile, the anti-hypertensive and anti-tumor activity of total triterpenoid sapogenins and their representative compound in bamboo, friedelin, have been systematically studied. These researches indicate that total triterpenoid sapogenins of the invention have extensive application prospect in the field of medicine, health food and daily cosmetics.

The invention is further illustrated by the following preferred examples, which are only intended to illustrate the invention, but not to limit the scope of the invention.

EXAMPLES

Example 1.A

Preparation of the Extract of *Phyllostachys nigra* var. *henonis*

5.5 kg bamboo shaving powders of *Phyllostachys nigra* var. *henonis* in Gramineae at the granularity of 20 meshes were put into the extraction kettle. The $CO_2$ pump was operated after the temperature reaching 55° C., thereby making $CO_2$ enter the extraction kettle by pre-heater when the pressure was risen to 30 Mpa. Meanwhile, the entrainer pump was operated in order to make 10% (v/v) acetone enter the extraction kettle simultaneously. The powder was dynamically extracted for 3 h. In addition, the separation pressure and temperature were set to 8 Mpa and 45° C. in No. 1 separation kettle, while in No. 2 separation kettle, the separation pressure and temperature were set to 5-6 Mpa and 27-30° C., respectively. Finally, the target product was taken out from No. 1 separation kettle and 121 g $EZR_{2002}$ were obtained after the product was cold dried and comminuted. The extraction yield was about 2.2%. Meanwhile, the entrainer was recovered from No. 2 separation kettle.

Example 1.B

Preparation of the Extract of *Phyllostachys pubescens*

The shoot sheaths of *Phyllostachys pubescens* in Gramineae were used as starting materials. They were extracted under the supercritical condition after dryness and comminution. The extraction temperature and pressure were set to 60° C. and 30 Mpa while the extraction time was set to 5 h. Meanwhile, the entrainer was 10% (v/v) ethanol. The other extraction conditions were the same as described in Example 1.A. The $EZR_{2002}$ extraction yield was about 0.98%.

Example 1.C

Preparation of the Extract of *Bambusa* Textiles MuClure

The complete stools of *Bambusa* textiles MuClure in *Bambusa* genus were used as starting materials. They were extracted unmodified with entrainers under the supercritical condition after dryness and comminution. The extraction temperature and pressure were set to 50° C. and 30 Mpa while the extraction time was set to 4 h. Meanwhile, the separation pressure and temperature in the separation kettle were set to 6 Mpa and 40° C., respectively. Finally, the target product was taken out and $EZR_{2002}$ was obtained after the product was cold dried and comminuted. The extraction yield was about 1.1%.

Example 2

Characterization of Bamboo Extract

In this example, the characteristics of the bamboo extract (Generally referred as "$EZR_{2002}$" in Example 1.A-1.C) obtained by $CO_2$ SFE technique were determined. The characteristics of extracts prepared in Example 1.A-1.C were same.

Figure 1:
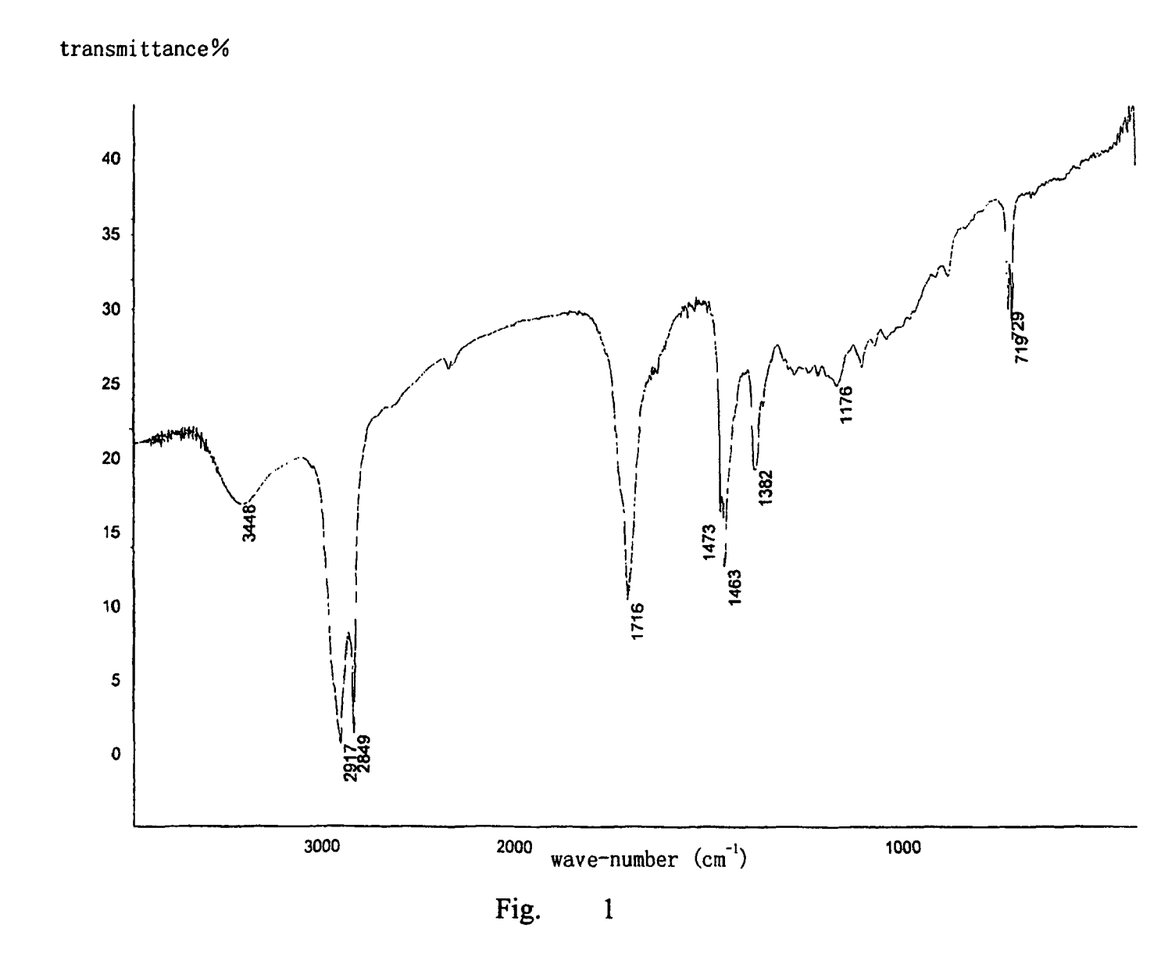
FIG. 1 shows the IR spectrogram of EZR2002 performed by potassium bromide.
Figure 2:
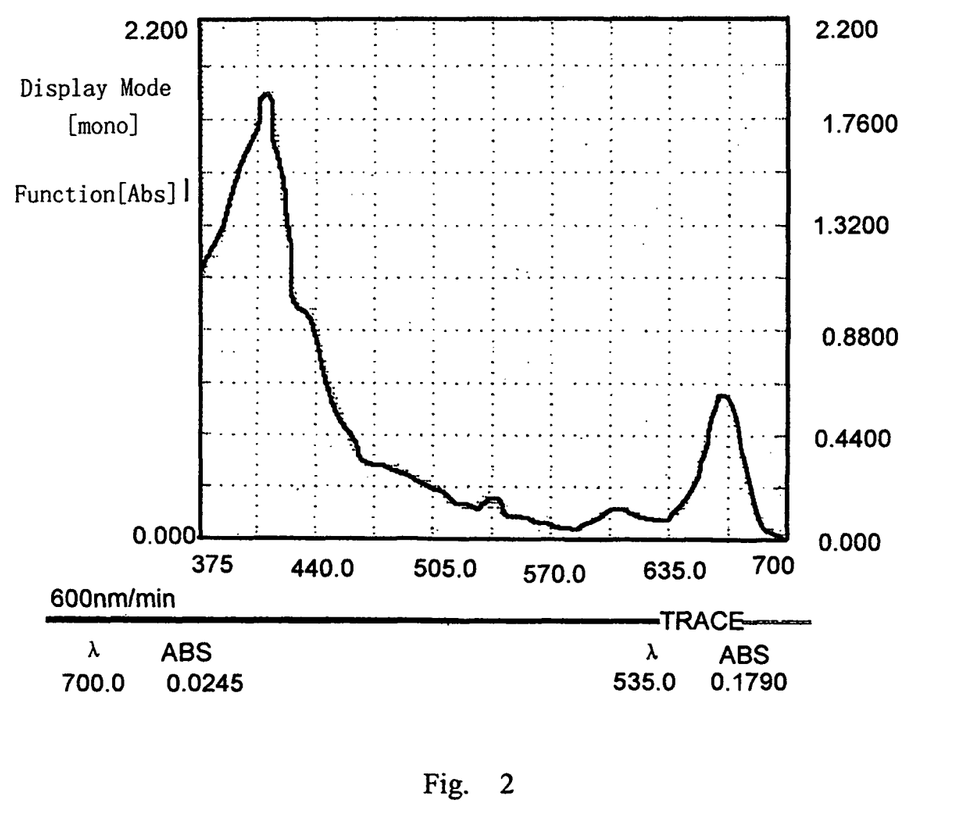
FIG. 2 shows the UV spectrogram of $EZR_{2002}$ dissolved by spectroscopic pure $CH_2Cl_2$.
Figure 3:
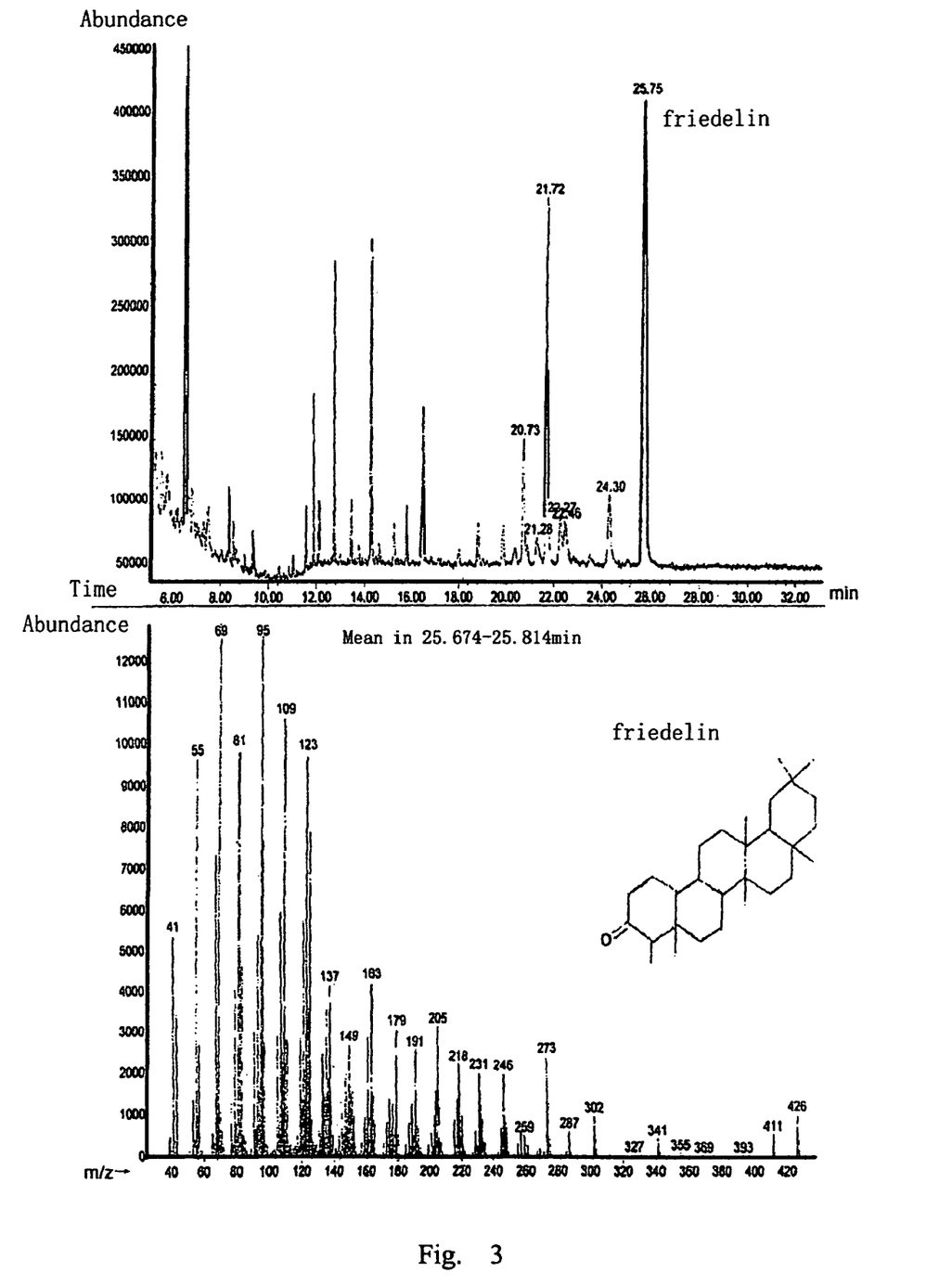
FIG. 3 shows the GC-MS chromatogram of $EZR_{2002}$ and the mass spectrogram of friedelin.
Figure 4:
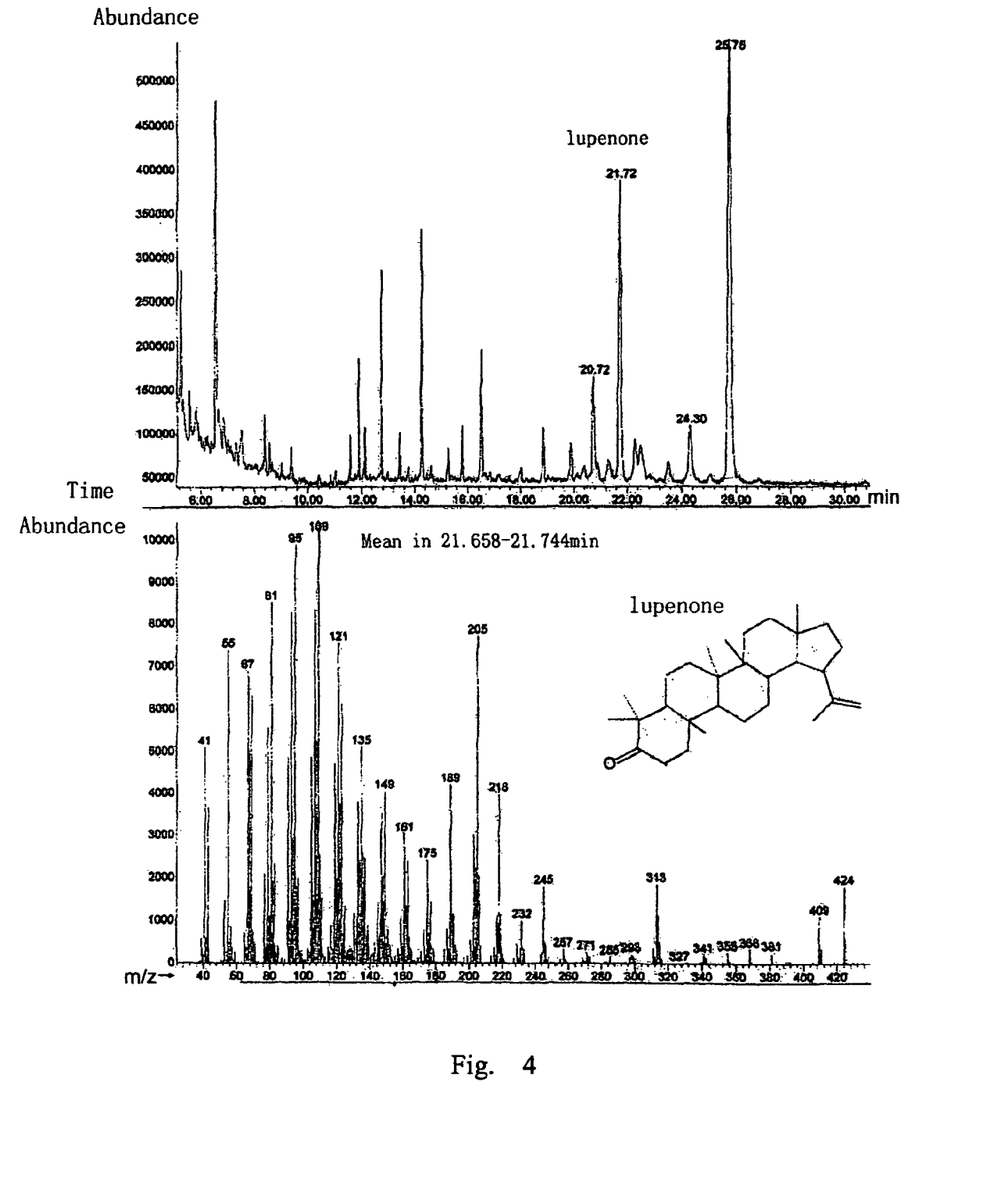
FIG. 4 shows the GC-MS chromatogram of $EZR_{2002}$ and the mass spectrogram of lupenone.
Figure 5:
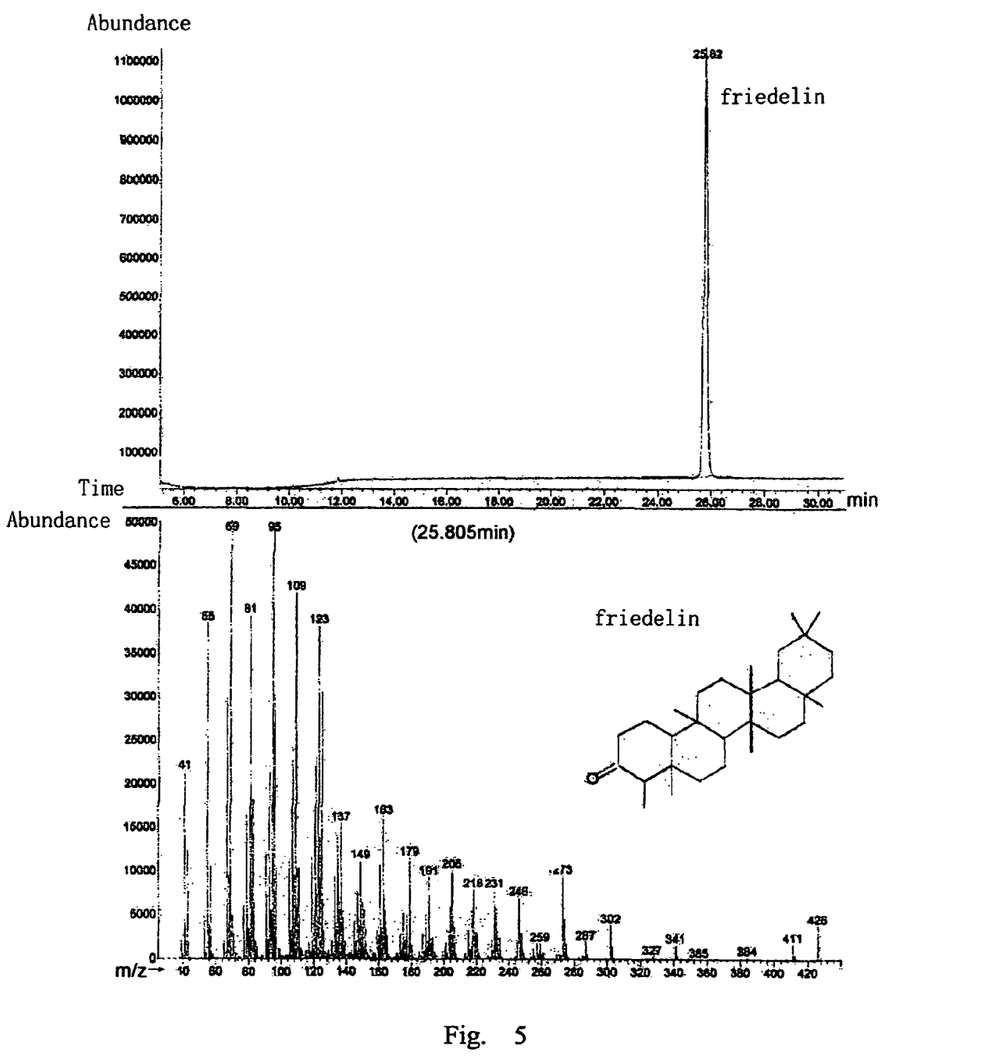
FIG. 5 shows the GC-MS chromatogram of friedelin standard.
Figure 6:
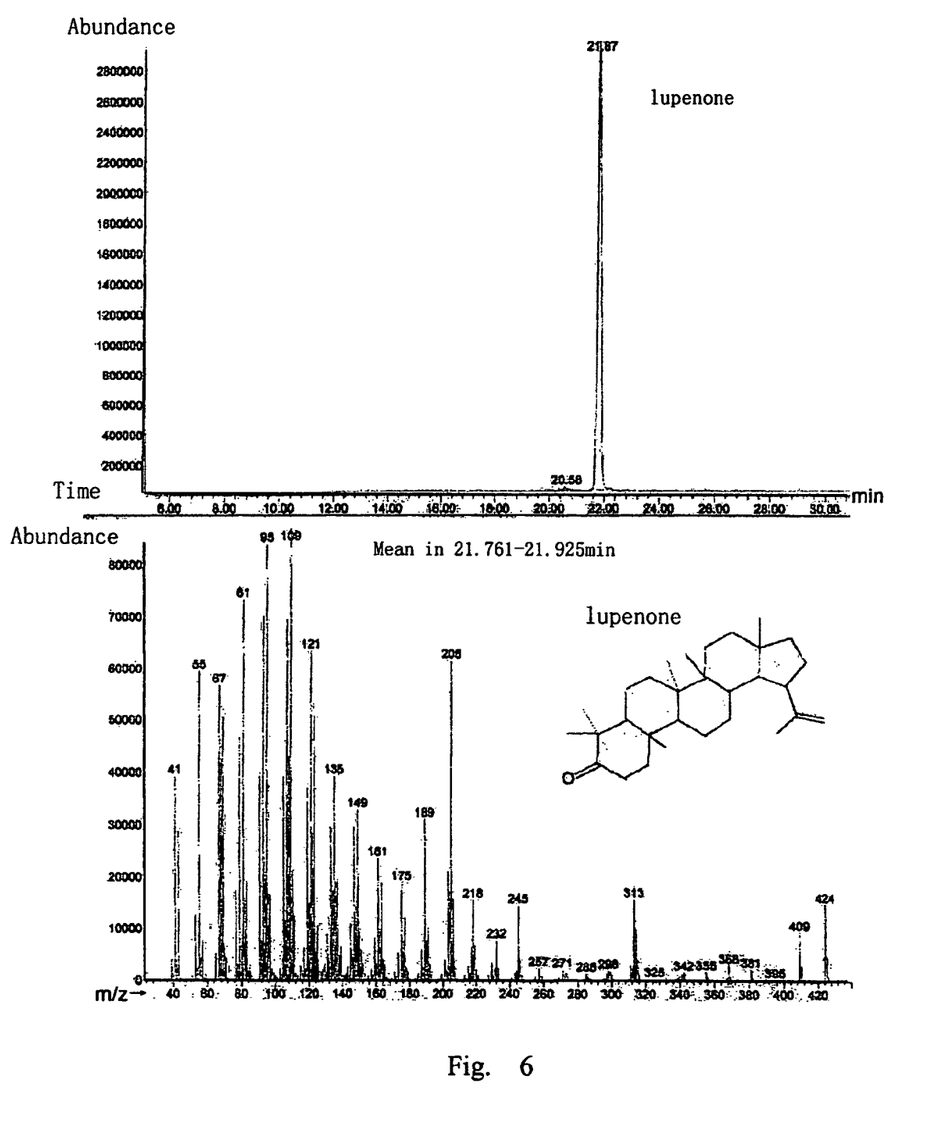
FIG. 6 shows the GC-MS chromatogram of lupenone standard.

$EZR_{2002}$ was identified as a group of pentacyclic triterpenoids of friedelin, lupenone and their homologous compounds. $EZR_{2002}$ was a kind of yellow or yellowish green powder and its melting point was between 74 and 79 degree C. The IR spectrogram of $EZR_{2002}$ performed by potassium bromide showed characteristic absorption peaks in the wavenumbers of 2917, 2849, 1716, 1463, 1382 and 720 $cm^{-1}$ (FIG. 1). The UV spectrogram of $EZR_{2002}$ dissolved by spectroscopic pure $CH_2Cl_2$ with a scan range from 300 to 700 nm showed a strong absorption in the wavelength of 412 nm, a sub strong absorption in the wavelength of 665 nm and a weak absorption in the wavelength of 505, 535 and 605 nm (FIG. 2).

The content of total triterpenoid sapogenins in different batches of $EZR_{2002}$ was determined between 55% and 75% by vanillic aldehyde and perchloric acid colorimetry using friedelin as a standard. The main free triterpenoids of $EZR_{2002}$ were determined as some pentacyclic triterpenoids such as friedelin, friedelan-3-β-ol, lupenone and lupeol detected by GC-MS. GC-MS analysis was performed by Hewlett-Packard (HP) 6890 gas chromatograph combined with a HP MS Engine 5973 mass spectrometer (Beckman, USA).

The GC conditions were as follows: The gas chromatograph was fitted with a HP5-MS column (30 m×0.25 mm I.D.) coated with a phenyl-methyl polysiloxane stationary phase (film thickness of 0.2 ↑m). Helium was used as carrier gas at a flow rate of 1 mL/min. 1 μL Sample was injected using splitless injection mode with the injection port temperature at 280° C. The column temperature was held at 100° C. for 2 min, then programmed from 100° C. to 270° C. at a rate of 20° C./min, holding 50 min.

The MS conditions were as follows: The mass selective detector was operated in the electron impact ionization mode with the ionization energy of 70 eV. The ion source temperature was 230° C. Full scan mode was used with the MS scan range from 18 to 500 m/z. Data were analyzed by Database NIST 98.

Compared to friedelin and lupenone standards (HPLC grade, Extrasynthese Co., Ltd, France), the contents of friedelin and lupenone in different batches of $EZR_{2002}$ quantitatively analyzed and detected by GC-MS were determined as $(20.2\pm5.2)\%$ and $(5.2\pm1.5)\%$, respectively. GC-MS chromatograms of $EZR_{2002}$ and two standards were shown in FIG. 3 through FIG. 6.

This invention also relates to the application of the bamboo extract (code name: $EZR_{2002}$), i.e. it was not only used to prepare drugs or health food on preventing cardiovascular diseases and carcinoma, but also used as the skin-protecting factor to apply in daily cosmetics. Examples 3 through 6 demonstrate various physiological and pharmacological activities of the extract described in the invention.

Example 3

Anti-Free Radical Activity of $EZR_{2002}$

The hydroxyl free radical (OH) produced by $Cu^{++}$-Vc-$H_2O_2$-Luminol-Yeast polysaccharides system was selected as index and measured by chemoluminescence method (Y. Zhang. Studies on antioxidative fraction in bamboo leaves and its capacity to scavenge active oxygen radicals, Journal of Bamboo Research, 1996, 15(3): 17-24). The $IC_{50}$ value of $EZR_{2002}$ for OH was determined as $(39.6\pm10.5)$ μg/mL by chemoluminescence method while the IC50 value of $EZR_{2002}$ for DPPH free radical was determined as $(300.4\pm50.6)$ μg/mL by colorimetric method. These results showed that $EZR_{2002}$ had notable activity of scavenging active oxygen radicals so that it had great potential in the application of bio-antioxidants.

Example 4

Anti-Hypertensive Activity of $EZR_{2002}$ in Spontaneous Hypertensive Rats 4.1. Materials The aqueous solution of $EZR_{2002}$ was fresh prepared for the concentrations of 20 and 60 mg/mL using Tween-80 as a solutizer just before the test. 20% of Tween-80 was given to rats as a control. In addition, the volume of $EZR_{2002}$ and Tween-80 for oral administration was 0.5 mL/100 g body weights.

18-week old male SHR with a body weight range from 300 to 365 g were obtained from Shanghai Experimental Animal Center of Chinese Academy of Sciences (Certificate of Qualification No. 152, Shanghai, China).

4.2. Methods

The blood pressure of each of conscious rats was measured by SHR electronic blood pressure meter (produced by Sino-Japan Friendship Hospital, Beijing, China). Rats were placed in an incubator at 38° C. and warmed for 15-20 min. The systolic pressure and heart rate of rats were measured by caudal artery indirect manometric method.

Two $EZR_{2002}$ dose groups and a hyperlipidemic control group were designed in this test. 18 rats were divided into three groups at random. $EZR_{2002}$ was given to rats at concentrations of 100 (low-dose group) and 300 (high-dose group) mg/kg body weight per day. Tween-80 was given to rats in the control group. The blood pressure of each SHR rat was measured in one week before oral administration. Official test was operated after a stable blood pressure. $EZR_{2002}$ was administrated orally one time for each day, continuous one week, at corresponding level to rats. The blood pressure of each rat was measured in the 1st, 4th and 7th day after administration. Furthermore, the blood pressure was measured four times, i.e. before administration and 2, 4, 6 h after administration in the 1st day. Results showed that the peak value time of $EZR_{2002}$ was 4-6 h. In the 4th and 7th day, the blood pressure was both measured twice, i.e. before administration (24 h after administration last time) and 4 h after administration.

4.3. Results

On one hand, the systolic pressure of SHR was $195\pm8$ mmHg at dose of 100 mg/kg per day by $EZR_{2002}$ in the 1st day before the test. Their values were $179\pm14$, $169\pm18$ and $165\pm19$ mmHg at 2, 4 and 6 h after administration, respectively. On the other hand, the systolic pressure of SHR was $199\pm7$ mmHg at dose of 300 mg/kg per day by $EZR_{2002}$ in the 1st day before the test. Their values were $188\pm12$, $181\pm14$ and $179\pm6$ mmHg at 2, 4 and 6 h after administration, respectively (Table 1). Furthermore, most of data in $EZR_{2002}$ dose groups had an obviously decline trend compared to the control group ($P<0.01$ and $P<0.05$).

TABLE 1

Effects of blood pressure in SHR at 2, 4 and 6 h in the 1st day after oral administration by $EZR_{2002}$ (Unit: mmHg, n = 6)

| Group | Treatment (mg/kg per day) | Before administration | Time after administration (h) 2 | 4 | 6 |
|---|---|---|---|---|---|
| Control | — | 191 ± 15 | 189 ± 13 | 193 ± 12 | 180 ± 11 |
| $EZR_{2002}$ | 100 | 195 ± 8 | 179 ± 14* | 169 ± 18** | 165 ± 19** |
| | 300 | 199 ± 7 | 188 ± 12 | 181 ± 14* | 179 ± 6** |

Compared to control, *P < 0.05, **P < 0.01.

Blood pressure values of SHR were $193\pm8$ and $189\pm20$ mmHg at doses of 100 and 300 mg/kg per day by $EZR_{2002}$ in the 4th day before administration, i.e. at 24 h in the 3rd day after administration, respectively. It had no significant difference compared to the control group ($190\pm18$ mmHg, $P>0.05$). Furthermore, their values were $184\pm13$ and $187\pm18$ mmHg at doses of 100 and 300 mg/kg per day by $EZR_{2002}$ in the 7th day before administration, i.e. at 24 h in the 6th day after administration, respectively. It had no significant difference compared to the control group ($187\pm20$ mmHg, $P>0.05$), either. These results suggested that the hold time of anti-hypertensive activity by $EZR_{2002}$ was less than 24 h (Table 2)

TABLE 2

Effects of blood pressure in SHR at 24 h after oral administration by EZR$_{2002}$ (Unit: mmHg, n = 6)

| Group | Treatment (mg/kg per day) | 1st day before ad. (Control) | 4th day before ad. (3rd day at 24 h after ad.) | 7th day before ad. (6th day at 24 h after ad.) |
|---|---|---|---|---|
| Control | — | 191 ± 15 | 190 ± 18 | 187 ± 20 |
| EZR$_{2002}$ | 100 | 195 ± 8 | 193 ± 8 | 184 ± 13 |
|  | 300 | 199 ± 7 | 189 ± 20 | 187 ± 18 |

Compared to control, P > 0.05.
ad. = administration.

The blood pressure of SHR at 4 h in the 1st, 4th and 7th day after administration had significant difference compared to the control group at doses of 100 and 300 mg/kg per day by EZR$_{2002}$ (P<0.01 and P<0.05, Table 3). Furthermore, the heart rate of SHR also had no significant change during the test (P>0.05, Table 4). In addition, the blood pressure of SHR in the control group had no significant change all the time during the whole test (P>0.05, Table 1, 2 and 3).

TABLE 3

Effects of blood pressure in SHR at 4 h in the 1st, 4th and 7th day after oral administration by EZR$_{2002}$ (Unit: mmHg, n = 6)

| | Treatment (mg/kg per day) | Before administration | Day after administration (d) | | |
|---|---|---|---|---|---|
| | | | 1 | 4 | 7 |
| Control | — | 191 ± 15 | 193 ± 12 | 180 ± 19 | 185 ± 25 |
| EZR$_{2002}$ | 100 | 195 ± 8 | 169 ± 18** | 165 ± 14** | 162 ± 9** |
| | 300 | 199 ± 7 | 181 ± 14* | 176 ± 19* | 178 ± 14* |

Compared to control, *P < 0.05, **P < 0.01. Blood pressure in SHR was measured at 4 h after each administration.

TABLE 4

Effects of heart rate in SHR at 4 h in the 1st, 4th and 7th day after oral administration by EZR$_{2002}$ (Unit: beat per 5 min, n = 6)*

| Group | Treatment (mg/kg per day) | Before administration | Day after administration (d) | | |
|---|---|---|---|---|---|
| | | | 1 | 4 | 7 |
| Control | — | 374 ± 77 | 391 ± 50 | 402 ± 55 | 424 ± 54 |
| EZR$_{2002}$ | 100 | 355 ± 42 | 332 ± 38 | 353 ± 69 | 399 ± 65 |
| | 300 | 357 ± 48 | 344 ± 30 | 395 ± 67 | 446 ± 37 |

*Compared to control, P > 0.05. Heart rate in SHR was measured at 4 h after each administration.

4.4. Conclusion

EZR$_{2002}$ had notable anti-hypertensive activity in Spontaneous Hypertensive Rats.

Example 5

Anti-Tumor Activity of EZR$_{2002}$ and its Main Element 5.1. EZR$_{2002}$ Anti-Tumor Active Filtration In Vitro
5.1.1~3. Methods Sulforhodamine B (SRB) protein staining method and microculture tetrozolium (MTT) reduction method were used to measure the growth inhibitory effects of tumor cells by EZR$_{2002}$ with the test objects of P$_{388}$ mouse leukemia cells and A$_{549}$ human lung adenocarcinoma cells, respectively. The effect time was 48 h and 72 h, respectively.

5.1.4. Active Evaluation Indices $10^{-5}$, $10^{-6}$ and $10^{-7}$ mol/L were determined as three critical levels. Invalid, weak effect and strong effect were determined as three evaluation indices.

| Sample level (mol/L) | Inhibition rate (%) | Evaluation indices |
|---|---|---|
| $10^{-5}$ | <85 | Invalid |
| $10^{-5}$ | > or =85 | Weak effect |
| $10^{-6}$ | >50 | |
| $10^{-6}$ | > or =85 | Strong effect |
| $10^{-7}$ | >50 | |

5.1.5. Results

Data were shown in Table 5 and 6.

TABLE 5

Inhibitory effects on the growth of P$_{388}$ mouse leukemia cells by EZR$_{2002}$*

| Sample level | | Inhibition rate (%) | | | | Evaluation |
|---|---|---|---|---|---|---|
| Vincristin (mol/L) | $10^{-4}$ 93.1 | $10^{-5}$ 94.3 | $10^{-6}$ 94.8 | $10^{-7}$ 94.7 | $10^{-8}$ 93.2 | Strong effects |
| EZR$_{2002}$ (mg/mL) | 1 90.7 | 0.25 98.2 | 0.063 90.4 | 0.016 57.7 | 0.004 0 | A little effects |

*MTT Reduction method. Effect time: 48 h.

TABLE 6

Inhibitory effects on the growth of A$_{549}$ human lung adenocarcinoma cells by EZR$_{2002}$*

| Sample level | | Inhibition rate (%) | | | | Evaluation |
|---|---|---|---|---|---|---|
| Vincristin (mol/L) | $10^{-4}$ 71.3 | $10^{-5}$ 71.6 | $10^{-6}$ 66.5 | $10^{-7}$ 44.3 | $10^{-8}$ 9.6 | Weak effects |
| EZR$_{2002}$ (mg/mL) | 1 70.2 | 0.25 90.6 | 0.063 24.8 | 0.016 0 | 0.004 0 | A little effects |

*SRB protein coloring method. Effect time: 72 h.

5.1.6. Conclusion

It was shown that EZR$_{2002}$ had inhibitory effect on P$_{388}$ mouse leukemia cells and A$_{549}$ human lung adenocarcinoma cells and also had anti-tumor activity.

5.2. Friedelin Extracted from $EZR_{2002}$ Anti-Tumor Test In Vitro

The Silica Gel Column Chromatography and Countercurrent Chromatography preparation techniques were used to obtain Friedelin monomer extracted from $EZR_{2002}$ for the sake of evaluating its anti-tumor activity further. The purity of this monomer determined by GC-MS analysis was 90.5%. MTT method operated by Major Laboratory of National Shenyang New Drug Security Evaluation (Shenyang Pharmaceutical University, Liaoning Province, China) was used to demonstrate the anti-tumor activity of friedelin monomer in vitro.

5.2.1. Cell Lines Selection $A_{375}$ (human malanoma), $L_{929}$ (mouse lung epithelial tumor), Hela (human cervical tumor) and THP-1 (human macrophage tumor) cell lines were used for active filtration test in this experiment. Among these cell lines, $A_{375}$, $L_{929}$ and Hela were adherent cells while THP-1 was a kind of suspended cell.

5.2.2. Materials and Culture Conditions

All cells were maintained in the RPMI-1640 culture medium supplemented with 10% fetal calf serum, penicillin (100 U/mL), streptomycin (100 µg/mL) and 0.2% $NaHCO_3$. These supplements were dissolved in deionized water and 0.22 µm filtration membrane was used for filter sterilization. The fetal calf serum was inactivated 30 min at 56° C. prior to an experiment. Cells were cultured in a humidified incubator of 5% $CO_2$ at 37° C.

5.2.3. Methods and Results $A_{375}$, $L_{929}$ and Hela cells in logarithmic growth phases were seeded at a cell density of approximately $5 \times 10^4$ cells/mL in 96 pore plates (100 µL/well). Furthermore, THP-1 cell was seeded at a cell density of approximately $1 \times 10^5$ cells/mL because it was smaller than others. Samples were added in suspended cells after culturing 4 h and in adherent cells after culturing 12 h. Friedelin was dissolved in DMSO in advance and then in the culture medium with the ultrasonic treatment, where the final concentration of the solvent in the culture medium was <0.1% (v/v). Sample was added for 7.5, 15, 30, 60, 120, 240, 480 and 960 µmol/L. Each level had four parallel pores and a negative control. The cells were incubated for 24 and 48 h and then 15 µL/well MTT solvent (5 mg/mL) was added.

The cells were incubated for 48 h, followed by centrifugation at 1500 rpm for 5 min. The supernatant was removed and 150 µL/well DMSO was added, followed by micro-vibrator shocking for 10 min and crystal dissolving completely. The absorbance (OD value) was measured by enzyme-labeled meter at 492 nm. Furthermore, the inhibitory rate of cell proliferation and the $IC_{50}$ value of friedelin were counted by using Bliss method. Results were shown in Table 7.

TABLE 7

The inhibitory rate and $IC_{50}$ values of four tumor cells by friedelin extracted from $EZR_{2002}$

| Sample level (µmol/L) | Inhibitory rate (%) | | | | | | | |
|---|---|---|---|---|---|---|---|---|
| | $A_{375}$ cell | | $L_{929}$ cell | | Hela cell | | THP-1 cell | |
| | 24 h | 48 h | 24 h | 48 h | 24 h | 48 h | 24 h | 48 h |
| 7.5 | 0 | 0.51 | 5.42 | 17.29 | 34.96 | 19.99 | 4.89 | 8.60 |
| 15 | 6.43 | 6.29 | 10.36 | 21.64 | 34.69 | 17.18 | 0 | 0 |
| 30 | 0.43 | 17.18 | 13.15 | 38.84 | 33.30 | 24.60 | 3.04 | 7.57 |
| 60 | 14.12 | 44.44 | 22.74 | 66.82 | 43.35 | 41.38 | 45.25 | 52.61 |
| 120 | 36.70 | 88.59 | 37.57 | 81.13 | 71.59 | 85.96 | 58.80 | 77.35 |
| 240 | 44.82 | 100.28 | 52.26 | 99.45 | 88.19 | 99.53 | 68.52 | 95.02 |
| 480 | 63.27 | 96.13 | 48.13 | 98.17 | 88.10 | 97.99 | 74.09 | 92.93 |
| 960 | 60.36 | 89.78 | 38.87 | 89.86 | 73.80 | 91.98 | 70.83 | 82.46 |
| $IC_{50}$ | 356.54 | 61.52 | 665.42 | 36.94 | 61.25 | 64.69 | 85.10 | 58.04 |

5.2.4. Comparison with the Positive Control

The de-methyl-cantharidin was taken as the positive control and the inhibitory rate of $A_{375}$, $L_{929}$ and Hela cells were measured by adding de-methyl-cantharidin (120 µmol/L) for 24 and 48 h (Table 8). Furthermore, the corresponding data of Friedelin were counted.

TABLE 8

The inhibitory rate (%) of three adherent tumor cells by Friedelin compared to de-methylcantharidin

| Sample* | $A_{375}$ cell | | $L_{929}$ cell | | Hela cell | |
|---|---|---|---|---|---|---|
| | 24 h | 48 h | 24 h | 48 h | 24 h | 48 h |
| De-methyl-cantharidin | 38.6 | 50.4 | 40.5 | 34.4 | 34.1 | 43.7 |
| Friedelin | 36.7 | 88.6 | 37.6 | 81.1 | 71.6 | 86.0 |

*The concentrations of both samples were 120 µmol/L.

5.2.5. Conclusion

Friedelin monomer extracted from $EZR_{2002}$ had inhibitory effects on the proliferation of four tumor cells, $A_{375}$ human lung adenocarcinoma cells, $L_{929}$ mouse lung epithelial tumor cells, Hela human cervical tumor cells and THP-1 human macrophage tumor cells to a different extent, with a time-dosage resistant relationship.

Friedelin had notable inhibitory effects on Hela and THP-1 cells at 24 h, which suggested that friedelin had higher sensitivity on these cells, but it had weaker sensitivity on $A_{375}$ and $L_{929}$ cells.

Compared to the positive control, de-methyl-cantharidin, friedelin displayed a rather strong anti-tumor activity so that it could be regarded as one of the most important active factors in $EZR_{2002}$. Meanwhile, it could be developed as anti-tumor drugs and health food.

Example 6

Skin Physiological Activity of $EZR_{2002}$

The efficiency test of skin physiological activity for $EZR_{2002}$ was operated by Skin Physiological and Toxicological Office of Research (School of Public Health, Fudan University) so that the application prospect in the field of daily cosmetics of $EZR_{2002}$ was systematically evaluated.

6.1. Materials and Methods 6.1.1. Sample Treatment $EZR_{2002}$ was dissolved in DMSO and sterilized by filter membrane method with the pore size of 0.22 µm. The sample solution was diluted with serum-free DMEM so that the final sequences of concentrations were adjusted to 0.5%, 0.05%, 0.005% and 0.0005%. Finally, they were stored at −4° C. and serum-free DMEM was selected as the control during the test.

6.1.2. Reagents and Containers

Several chemical and biochemical reagents including K-SFM culture medium (Gibcol Co., Ltd. USA), DMEM culture medium, insulin, fetal calf serum (NBS), hydrocortisone, penicillin, streptomycin, trypsinase and ficoll were selected in this test. Meanwhile, some containers including 96-pore plate, 24-pore plate, 35 mm culture dish and 25 cm2 culture flask (Corning Co., Ltd. USA) were also used in the test.

6.1.3. Instruments

Instruments used in this test were as follows: enzyme-labeled meter (BIO-TEK Co., Ltd.), pH meter, super-clean bench, incubator and 722 spectrophotometer.

6.1.4. Primary Culture of Skin Cells

The back skin was obtained from three-day natal SD rats and skin epidermal keratinocytes cultured in K-SFM culture medium were prepared with 0.25% trypsinase by cold digestion method. Cells were seeded in 96 and 24 pore plate at a cell density of approximately $1 \times 10^6$ cells/mL. In addition, the culture medium was changed at 24 h for the first time while it was changed every other 2-3 days subsequently. Finally, the sample was added when the cultured cells grew to 80% confluence.

6.1.5. Determination of Lipid Peroxidation Product (i.e. Malondialdehyde, MDA) and Superoxide Dismutase (SOD)

MDA and SOD were determined by thiobarbituric acid (TBA) colorimetric method and nitrite reduction method, respectively. The reagent box was brought from Nanjing Jiancheng Bioengineering Institute (Jiangsu Province, China).

6.1.6. Safety Evaluation Test

The assessment procedure and method were operated according to Health Standards of Cosmetics (1999 Edition, Ministry of Health P. R. China). Furthermore, the sample level was set to 10%. (i) Skin stimulus test: 0.2 mL sample was coated on the skin in an hour every day and continuously 14 days. (ii) Eye stimulus test: 0.1 mL sample was dropped into conjuctival saccus and animal eyes were examined at 1 h, 24 h, 48 h, 72 h, 4th day and 7th day after toxicant exposure.

6.2. Results 6.2.1. Effect of Retarding Skin Senescence

MDA level of skin cells was significantly reduced by $EZR_{2002}$ at the dose range of 0.0005%-0.005%, i.e. 5-50 mg/kg body weight, compared to the control group while SOD activity was significantly intensified compared to the control group (Table 9).

TABLE 9

Effect of MDA level and SOD activity of skin keratinocytes by $EZR_{2002}$

| Sample level (%) | MDA level (nmol/mL) | SOD activity (U/mL) |
|---|---|---|
| Control | 1.66 ± 0.22 | 2.94 ± 0.085 |
| 0.0005 | 0.60 ± 0.21** | 3.21 ± 0.081* |
| 0.005 | 0.58 ± 0.33** | 3.36 ± 0.024* |
| 0.05 | 2.66 ± 0.42 | 2.43 ± 0.12 |
| 0.5 | 4.60 ± 0.67 | 0.93 ± 0.47 |

*Compared to control, *P < 0.05, **P < 0.01.

6.2.2. Safety Evaluation

Negative results in skin and eye stimulus test showed no skin and eye stimulation.

6.3. Conclusion $EZR_{2002}$ had rather strong activity of anti oxidant-induced injury at a dose range of 5-50 mg/kg body weight. It not only intensified SOD activity of skin, but also reduced MDA level. Therefore, $EZR_{2002}$ had good physiological efficiency of protecting skin and hair so that it could be widely applied in the field of daily cosmetics.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A method of treating hypertension comprising administering to a subject suffering from said hypertension a therapeutically effective amount of total triterpenoid sapogenins extracted from bamboo shaving powder by mixing the bamboo shaving powder with supercritical $CO_2$ fluid at temperature 50-60 degree C. and pressure 25-35 Mpa for 2-5 hours, wherein the total triterpenoid sapogenins is 10-90% of the composition as determined by vanillic aldehyde and perchloric acid colorimetry using friedelin as a standard, said total triterpenoid sapogenins comprising 5-35% friedelin and 1-10% lupenone as determined by GC-MS, said therapeutically effective amount of total triterpenoid sapogenins is administered orally in medicine or food.

2. A method for intensifying Superoxide Dismutase (SOD) activity or reducing Malondialdehyde (MDA) level of the skin or hair in a subject comprising administering to a subject a therapeutically effective amount of total triterpenoid sapogenins extracted from bamboo shaving powder by mixing the bamboo shaving powder with supercritical $CO_2$ fluid at temperature 50-60 degree C. and pressure 25-35 Mpa for 2-5 hours, wherein the total triterpenoid sapogenins is 10-90% of the composition as determined by vanillic aldehyde and perchloric acid colorimetry using friedelin as a standard, said total triterpenoid sapogenins comprising 5-35% friedelin and 1-10% lupenone as determined by GC-MS to intensify SOD activity or to reduce MDA level of the skin or hair, wherein said therapeutically effective amount of total triterpenoid sapogenins is administered externally onto the skin or hair in a daily cosmetic.

3. A method of inhibiting growth of cancer cells or tumor cells, comprising treating the cancer cells or tumor cells a therapeutically effective amount of total triterpenoid sapogenins extracted from bamboo shaving powder by mixing the bamboo shaving powder with supercritical $CO_2$ fluid at temperature 50-60 degree C. and pressure 25-35 Mpa for 2-5 hours, wherein the total triterpenoid sapogenins is 10-90% of the composition as determined by vanillic aldehyde and perchloric acid colorimetry using friedelin as a standard, said total triterpenoid sapogenins comprising 5-35% friedelin and 1-10% lupenone as determined by GC-MS.

4. The method according to claim 3, wherein the total triterpenoid sapogenins is pentacyclic triterpenoid sapogenins.

* * * * *

UNITED STATES PATENT AND TRADEMARK OFFICE
CERTIFICATE OF CORRECTION

PATENT NO. : 7,811,997 B2  Page 1 of 1
APPLICATION NO. : 10/538463
DATED : October 12, 2010
INVENTOR(S) : Ying Zhang et al.

It is certified that error appears in the above-identified patent and that said Letters Patent is hereby corrected as shown below:

Title page, item (73) Assignee:
Zhang; Ying (~~Baiyur~~ Villa, Hangzhou, Zhejiang, CN)

should be corrected as:

Zhang; Ying (<u>Baiyun</u> Villa, Hangzhou, Zhejiang, CN)

Signed and Sealed this
Nineteenth Day of April, 2011

David J. Kappos
*Director of the United States Patent and Trademark Office*